(12) United States Patent
Roper et al.

(10) Patent No.: US 10,586,692 B2
(45) Date of Patent: Mar. 10, 2020

(54) METHODS OF MULTIPLEXING SAMPLE ANALYSIS BY MASS SPECTROMETRY

(71) Applicants: Florida State University Research Foundation, Inc., Tallahassee, FL (US); St. Louis University, St. Louis, MO (US)

(72) Inventors: Michael G. Roper, Tallahassee, FL (US); James L. Edwards, St. Louis, MO (US)

(73) Assignees: Florida State University Research Foundation, Inc., Tallahassee, FL (US); St. Louis University, St. Louis, MO (US)

( * ) Notice: Subject to any disclaimer, the term of this patent is extended or adjusted under 35 U.S.C. 154(b) by 0 days.

(21) Appl. No.: 16/167,806

(22) Filed: Oct. 23, 2018

(65) Prior Publication Data

US 2019/0122874 A1  Apr. 25, 2019

Related U.S. Application Data

(60) Provisional application No. 62/575,844, filed on Oct. 23, 2017.

(51) Int. Cl.

| | | |
|---|---|---|
| *H01J 49/00* | (2006.01) | |
| *H01J 49/16* | (2006.01) | |
| *G01N 30/72* | (2006.01) | |
| *H01J 49/42* | (2006.01) | |
| *H01J 49/04* | (2006.01) | |
| *G01N 30/62* | (2006.01) | |

(52) U.S. Cl.
CPC ........ *H01J 49/009* (2013.01); *G01N 30/7266* (2013.01); *H01J 49/0027* (2013.01); *H01J 49/0036* (2013.01); *H01J 49/0431* (2013.01); *H01J 49/165* (2013.01); *H01J 49/4225* (2013.01); *G01N 30/7233* (2013.01); *G01N 2030/623* (2013.01)

(58) Field of Classification Search
CPC ........ H01J 49/00; H01J 49/02; H01J 49/0027; H01J 49/0031; H01J 49/0431; H01J 49/009
USPC ......................................... 250/281, 282, 288
See application file for complete search history.

(56) References Cited

U.S. PATENT DOCUMENTS

| | | | | |
|---|---|---|---|---|
| 2006/0118713 A1* | 6/2006 | Matsui | ............... | G01N 30/7266 250/288 |
| 2013/0295597 A1* | 11/2013 | DeWitte | ................. | G01N 30/06 435/23 |

OTHER PUBLICATIONS

Allen, P.B., et al. "Fourier Transform Capillary Electrophoresis with Laminar-Flow Gated Pressure Injection," Analytical Chemistry. 2007;79(17):6807-15.

Azizi, F. et al., "Generation of Dynamic Chemical Signals with Pulse Code Modulators," Lab Chip. 2008;8(6):907-12.

(Continued)

*Primary Examiner* — Jason L McCormack
(74) *Attorney, Agent, or Firm* — Eversheds Sutherland (US) LLP

(57) ABSTRACT

Provided herein are methods for multiplexed sample analysis by mass spectrometry. The methods may be performed without the need for chemical tagging. The methods also may include the analogous use of frequency modulation to multiplex mass spectrometric analysis, which may be referred to as frequency-modulated continuous flow analysis electrospray ionization mass spectrometry (FM-CFA-ESI-MS).

17 Claims, 10 Drawing Sheets

(56) References Cited

OTHER PUBLICATIONS

Dongre, C, et al., "Modulation-Frequency Encoded Multi-color Fluorescent DNA ANalysis in an Optofluidic Chip," Lab on a Chip. 2011;11(4):679-83.
Edel, H. et al., "Frequency-modulated Simultaneous Atomic Absorption Spectrometry (FremsAAS): Determination of As, Se and Sb," Anal. Bioanal. Chem. 1996; 355:292-4.
Fernandez, F.M. et al. "Hadamard Transform Time-of-Flight Mass Spectrometry: A High-Speed Detector for Capillary-Format Separations," Anal. Chem. 2002;74(7):1611-7.
Kaneta, T. et al., "Hadamard Transform Capillary Electrophoresis," Analytical Chemistry 1999;71(23):5444-6.
Knorr, F.J. et al. "Fourier Transform Ion Mobility Spectrometry," Anal. Chem. 1985;57(2):402-6.
Kwok, Y.C. et al., "Shah convolution differentiation Fourier transform for rear analysis in microchip capillary electrophoresis," J. Chromatogr. A. 2001;924(1-2):177-86.
Trudgett, M.J., et al., "Theoretical Description of a New Analytical Technique: Compreshensive ONline Multidimensional Fast Fourier Transform Separations," J. Chromatogr. A. 2011;1218(22):3545-54.
Xie, Y. et al., "Fourier Microfluidics," Lab Chip. 2008;8(5):779-85.
Zhang, X.Y. et al. "Microfluidic System for Generation of Sinusoidal Glucose Waveforms for Entrainment of Islets of Langerhans," Anal. Chem., 2010;82(15):6704-11.

* cited by examiner

METHODS OF MULTIPLEXING SAMPLE ANALYSIS BY MASS SPECTROMETRY

CROSS-REFERENCE TO RELATED APPLICATIONS

This application claims priority to U.S. Provisional Patent Application No. 62/575,844, filed Oct. 23, 2017, which is incorporated herein by reference.

BACKGROUND

As chemical and biological sample complexity has grown, analytical techniques have evolved to maintain accuracy and precision of final results. These techniques often include running multiple calibration curves throughout the day with multiple controls. One way to increase throughput and efficiency is to analyze multiple samples at the same time, which is typically referred to as multiplexing. Multiplexing generally may include the analysis of multiple samples simultaneously.

Sample throughput can be achieved using either parallel or serial multiplexing. In serial approaches, samples are run one after another. By decreasing the time of each individual analysis, the number of samples that can be analyzed is increased. In parallel approaches, multiple samples are run simultaneously. While the length of a single experiment may be longer than that for a serial approach, this can be offset by the ability to analyze multiple samples at one time.

Mass spectrometry (MS) typically achieves sample multiplexing through chemical tagging approaches using a variety of isotope labeling schemes. Using these approaches, parallel multiplexing of up to 10 samples may be possible, although often fewer samples are run simultaneously. These methods also provide advantages in quantitation because differences in ionization efficiency/signal response between samples can be normalized because they are analyzed simultaneously, which accounts for the matrix heterogeneity of each sample. Therefore, even though competing ionization and signal suppression may occur, these phenomena should be experienced equally by all of the samples.

These approaches, however, typically suffer from one or more disadvantages, such as the one or more difficulties associated with the labeling chemistry that is required to covalently attach a tag to the analytes. The reactions usually are directed to specific functional groups, but these specific functional groups may not be present on all compounds of interest. Tagging efficiencies also can vary between samples and/or between analytes within each sample. Another disadvantage is the cost of at least some of these reagents.

Frequency-modulation (FM) is one approach to multiplexing in which each sample may be encoded at a particular frequency. The total signal detected by the instrument may then be a sum of all the frequency components in the mixture, and deconvolution by Fourier transform (FT) can reveal its unique spectral components. Therefore, the identity of each sample may be encoded by its unique frequency and its concentration may be encoded by the peak height in the frequency domain. Besides the ability for parallel multiplexing, one possible advantage of this method is that it inherently filters the signal since the frequency of each component can be modulated away from noise and selected with appropriate bandwidths. Combined, these benefits often result in an increased S/N.

For optical measurements, FM multiplexing has been achieved by modulating the intensities of multiple light sources at unique frequencies. The emission from each compound can then be encoded at the frequency that was used to excite it. One demonstration of this method was used in the determination of multiple elements simultaneously using atomic absorption spectroscopy (see Edel H. et al., Anal. Bioanal. Chem. 1996; 355:292-4). In this approach, the power of three hollow cathode lamps and a deuterium lamp were modulated independently at unique frequencies. Lock-in amplifiers were used to monitor the signal from each source independently of the other sources and background emission from the furnace. This technique has been used to analyze 11 elements simultaneously. In another example of FM multiplexing, two lasers were pulsed at unique frequencies for simultaneous measurement of two DNA samples that were being separated by electrophoresis (see Dongre C, et al., Lab on a Chip. 2011; 11(4):679-83).

One technique particularly suited for analyzing multiple analytes in a single run is mass spectrometry (MS). One of the most common methods for multiplexing samples for analysis by MS is through incorporation of tags into one, or multiple, samples. For example, stable isotope labeling by amino acids in cell culture (SILAC), isotope coded affinity tags, and isobaric tags for relative and absolute quantification (iTRAQ™, Applied Biosystems, USA). iTRAQ™, which utilizes covalent labeling of primary amines with isobaric tags, can enable multiplexing and relative quantitation of up to 8 different samples.

Other techniques that utilize a frequency-based approach for increasing the throughput of a single sample and thereby increase S/N of the measurement include the following: FT-ion mobility spectroscopy (FT-IMS)(see Knorr, F. J. et al., Anal. Chem. 1985; 57(2):402-6), Hadamard Transform Time-of-Flight MS (HT TOF-MS) (see Fernandez, F. M. et al., Anal. Chem. 2002; 74(7):1611-7), Hadamard Transform capillary electrophoresis (HT-CE)(see Kaneta, T. et al., Analytical Chemistry 1999; 71(23):5444-6), Shah convolution FT detection (SCOFT) (see Kwok, Y. C. et al., J. Chromatogr. A. 2001; 924(1-2):177-86), FT-CE (see Allen, P B, et al., Analytical Chemistry. 2007; 79(17):6807-15), or a general fast Fourier transform separation (see Trudgett, M. J., et al., J. Chromatogr. A. 2011; 1218(22):3545-54). While each of these systems are unique in the way in which they utilize frequency-based approaches for increasing S/N, they are all configured to analyze a single sample.

Each of these methods suffers from one or more disadvantages, including, but not limited to, their cost, the diligence required to achieve similar labeling efficiencies, possible background interference, and the one or more inefficiencies associated with the ability to analyze a single sample.

There remains a need for a relatively inexpensive and/or non-labeling approach for parallel and/or serial multiplexing by MS. There also remains a need for methods that avoid or reduce background interference, eliminate or reduce one or more difficulties associated with achieving similar labeling efficiencies, analyze two or more samples, or a combination thereof.

BRIEF SUMMARY

Provided herein are methods that meet one or more of the foregoing needs, including methods that allow quantitation regardless of functional group composition.

In some embodiments, the methods provided herein utilize a frequency-modulated (FM) approach to sample multiplexing. For example, each sample may be encoded at unique frequencies prior to detection of a total signal by MS, and reconstructed ion chromatograms (RIC) at each m/z of interest may then be a time-dependent signal which is composed of the unique frequencies from each sample. Deconvolution of the RIC by a technique, such as Fourier transform (FT), may reveal the identity of the sample, its relative concentration, or a combination thereof.

In one aspect, methods of mass spectrometric analysis of a sample are provided. In some embodiments, the methods include providing a first liquid at a first flow rate that is varied at a first frequency, wherein the first liquid includes at least one first analyte; providing a second liquid at a second flow rate that is varied at a second frequency, wherein the second liquid includes at least one second analyte, and wherein the first frequency and the second frequency are different; combining the first liquid and the second liquid with a third liquid to form a combined liquid, wherein the third liquid has a time-dependent velocity effective to impart the combined liquid with a substantially constant flow rate; analyzing the combined liquid with a mass spectrometer to monitor one or more selected m/z ratios; collecting one or more reconstructed ion chromatograms for the one or more selected m/z ratios; and analyzing the one or more reconstructed ion chromatograms to determine (i) which of the at least one first analyte and/or the at least one second analyte contributed to a signal, (ii) the relative concentration of the at least one first analyte and/or the at least one second analyte that contributed to the signal, or (iii) a combination thereof.

Additional aspects will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Figure 1:
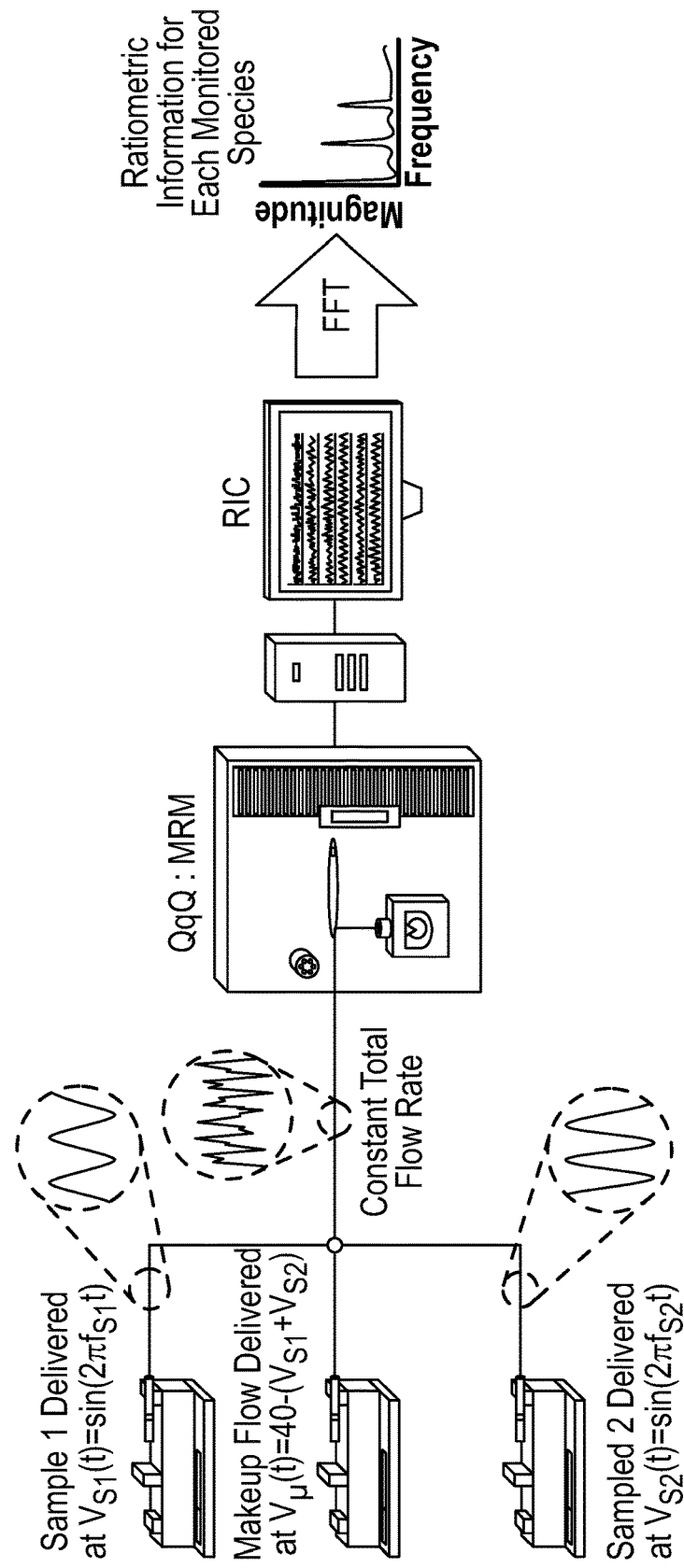
FIG. 1 depicts an embodiment of a system for performing embodiments of the methods described herein.

Provided herein are methods for multiplexed sample analysis by mass spectrometry. The methods provided herein include both serial and parallel multiplexing by mass spectrometry (MS). In some embodiments, the methods are performed without the need for chemical tagging. Therefore, one or more problems associated with chemical labeling, such as inefficiencies, side products, or a combination thereof, may be reduced or avoided.

The methods provided herein may be used for multiplexing multiple samples by MS. In some embodiments, the methods provided herein can be used to analyze multiple samples without the use of isotopes.

Not wishing to be bound by any particular theory, it is believed that the methods provided herein may lead to increased gains in sample throughput and, therefore, data collection in numerous fields, thereby positively impacting the users of the technology, as well as those who would benefit indirectly from its incorporation, for example, by lowering costs.

In some embodiments, more than 4 samples can be analyzed simultaneously in the methods provided herein, as long as the unique frequencies of the samples can be resolved in the frequency domain and the analytes of the samples are within the dynamic range of the mass spectrometer.

In some embodiments, the methods apply frequency modulation to multiplex mass spectrometric analysis, which may be referred to herein as frequency-modulated continuous flow analysis electrospray ionization mass spectrometry (FM-CFA-ESI-MS).

In some embodiments, each sample is pulsed at a specific frequency, and then combined with each other and a make-up flow of buffer. The make-up flow may be used to ensure a constant total flow rate of solution to an electrospray ionization source. In some embodiments, analysis of reconstructed ion chromatograms at one or more selected m/z ratios may reveal a time-dependent ion trace that is a superposition of the various sample frequencies. Spectral deconvolution of these traces can reveal which sample contributed to the signal, through which frequencies are present, and their relative concentrations, through the ratio of peak heights.

First Liquid and Second Liquid

In some embodiments, the methods provided herein include providing a first liquid at a first flow rate that is varied at a first frequency, wherein the first liquid comprises at least one first analyte; and providing a second liquid at a second flow rate that is varied at a second frequency, wherein the second liquid comprises at least one second analyte, and wherein the first frequency and the second frequency are different.

The first liquid and the second liquid may independently include an organic liquid, water, or a combination thereof. The organic liquid may be one in which the one or more analytes of the first liquid and/or second liquid are soluble. In some embodiments, the first liquid includes acetonitrile and water. In some embodiments, the second liquid includes acetonitrile and water.

The first liquid generally includes at least one first analyte, and the second liquid generally includes at least one second analyte. The number of analytes in the first liquid and the second liquid may be limited only by the ability of a mass spectrometer to resolve the analytes. In some embodiments, the first liquid includes 2 to 300 analytes, 2 to 250 analytes, 2 to 200 analytes, 2 to 150 analytes, 2 to 100 analytes, 2 to 75 analytes, 2 to 50 analytes, 2 to 25 analytes, or 2 to 9 analytes. In some embodiments, the second liquid includes 2 to 300 analytes, 2 to 250 analytes, 2 to 200 analytes, 2 to 150 analytes, 2 to 100 analytes, 2 to 75 analytes, 2 to 50 analytes, 2 to 25 analytes, or 2 to 9 analytes. The number of the analytes in the first liquid and the second liquid may be the same or different.

Generally, the analytes may be present in the first liquid and the second liquid at any concentration that does not undesirably impact the methods described herein. In some embodiments, the concentration of at least one first analyte of the first liquid and the concentration of at least one second analyte of the second liquid are different. The concentration of the at least one first analyte and the concentration of the at least one second analyte may be independently selected from a concentration of about 10 µM to about 100 µM, about 10 µM to about 75 µM, about 10 µM to about 50 µM, about 10 µM to about 40 µM, about 20 µM to about 30 µM, or about 25 µM.

In some embodiments, the at least one first analyte and the at least one second analyte are different. In some embodiments, the at least one first analyte and the at least one second analyte are identical. The first liquid and the second liquid may include one or more of the same analytes. All or a portion of the analytes of the first liquid may be identical to those of the second liquid.

Generally, the at least one first analyte and the at least one second analyte may be independently selected from any material that is soluble in the first liquid or second liquid, respectively. In some embodiments, the at least one first analyte, the at least one second analyte, or a combination thereof includes an amino acid, a perfluorinated acid, or a combination thereof. The amino acid may be a natural or synthetic amino acid. In some embodiments, the at least one first analyte, the at least one second analyte, or a combination thereof includes an organic molecule having a molecule weight less than or equal to 500 g/mol.

The first liquid generally may be provided at a first flow rate having a first frequency. The first frequency may be imparted by sinusoidally modulating the first flow rate from a first rate to a second rate for a selected period. In other words, the flow is started at a first flow rate (e.g., 3.3 µL/minute), increased to a second flow rate (e.g., 16.7 µL/minute), and then decreased to the first flow rate, all in one period (e.g., 97 seconds). In some embodiments, the first frequency is imparted by sinusoidally modulating the first flow rate from (i) about 1 µL/minute to about 10 µL/minute to (ii) about 11 µL/minute to about 25 µL/minute with a period of about 80 seconds to about 120 seconds. In some embodiments, the first frequency is imparted by sinusoidally modulating the first flow rate from (i) about 1 µL/minute to about 5 µL/minute to (ii) about 12 µL/minute to about 18 µL/minute with a period of about 90 seconds to about 110 seconds. In some embodiments, the first frequency is imparted by sinusoidally modulating the first flow rate from 3.3 µL/minute to about 16.7 µL/minute with a period of about 97 seconds.

The second liquid generally may be provided at a second flow rate having a second frequency. The second frequency may be imparted by sinusoidally modulating the second flow rate from a first rate to a second rate over a selected period. In some embodiments, the second frequency is imparted by sinusoidally modulating the second flow rate from (i) about 1 µL/minute to about 10 µL/minute to (ii) about 11 µL/minute to about 25 µL/minute with a period of about 20 seconds to about 60 seconds. In some embodiments, the second frequency is imparted by sinusoidally modulating the second flow rate from (i) about 1 µL/minute to about 5 µL/minute to (ii) about 12 µL/minute to about 18 µL/minute with a period of about 30 seconds to about 50 seconds. In some embodiments, the second frequency is imparted by sinusoidally modulating the second flow rate from 3.3 µL/minute to about 16.7 µL/minute with a period of about 43 seconds.

One or more additional analyte-containing liquids may be tested in the methods described herein. In some embodiments, the methods includes providing one or more additional liquids. Each of the one or more additional liquids includes one or more additional analytes, and each of the one or more additional liquids has a flow rate that is varied at a unique frequency that differs from both (i) the first frequency and (ii) the second frequency; and combining the at least one additional liquid with the third liquid to form the combined liquid. When one or more additional analyte-containing liquids are tested in the methods described herein, the one or more reconstructed ion chromatograms may be analyzed to determine (i) which of the at least one first analyte, the at least one second analyte, the one or more additional analytes, or a combination thereof contributed to a signal, (ii) the relative concentration of the at least one first analyte, the at least one second analyte, the one or more additional analytes, or a combination thereof that contributed to the signal, or (iii) a combination thereof.

In some embodiments, the methods include combining with the third liquid 1 to 8 additional analyte-containing liquids, each including at least one analyte and having a flow rate that is varied at a unique frequency that differs from the first frequency and the second frequency. In other words, the frequency of the flow rate of each additional analyte-containing liquid differs from the first frequency, the second frequency, and the frequency of each of the other additional analyte-containing liquids that may be present. Therefore, any number of additional liquid having different frequencies may be analyzed according to the methods provided herein.

Not wishing to be bound by any particular theory, it is believed that the quantitation of any number of analyte-containing liquids may be possible with the caveat, at least in some embodiments, that the dynamic range of the mass spectrometer determines the maximum number of samples that can be multiplexed.

In some embodiments, the ability to quantitate analytes from each liquid (e.g., first liquid, second liquid, one or more additional analyte-containing liquids), according to some embodiments herein, is substantially independent of the salt concentration in the liquids, likely due to the fact that the liquids are mixed together and analyzed simultaneously. More specifically, embodiments of the methods provided herein demonstrate resistance to diminished quantitation due to salting effects, likely due, at least in some embodiments, to the mixing of the sample buffers before ESI, which may result in similar salt concentrations for all samples under analysis.

Third Liquid

The methods provided herein may include combining the first liquid and the second liquid (and, in some embodiments, one or more additional liquids) with a third liquid to form a combined liquid, wherein the third liquid has a time-dependent velocity effective to impart the combined liquid with a substantially constant flow rate.

The third liquid generally may include any liquid that does not undesirably impact the methods described herein. For example, the third liquid may include a liquid that does not or is unlikely to react with an analyte during the methods described herein. In some embodiments, the third liquid includes a buffer. In some embodiments, the third liquid includes a 50:50 acetonitrile:aqueous 0.1% formic acid solution.

The third liquid may be combined with the other liquids of the methods described herein, including the first liquid and the second liquid, to form a combined liquid, and the combined liquid may a substantially constant flow rate. For example, the third liquid may be provided with a time-dependent velocity that neutralizes the flow rate frequencies of the other liquids, such as the first liquid and the second liquid. The substantially constant flow rate may include any flow rate that does not undesirably impact the methods described herein.

In some embodiments, the substantially constant flow rate of the combined liquid is about 1 µL/minute to about 100 µL/minute. In some embodiments, the substantially constant flow rate of the combined liquid is about 10 µL/minute to about 90 µL/minute. In some embodiments, the substantially constant flow rate of the combined liquid is about 10 µL/minute to about 80 µL/minute. In some embodiments, the substantially constant flow rate of the combined liquid is about 10 µL/minute to about 70 µL/minute. In some embodiments, the substantially constant flow rate of the combined liquid is about 20 µL/minute to about 60 µL/minute. In some embodiments, the substantially constant flow rate of the combined liquid is about 30 µL/minute to about 50 µL/minute. In some embodiments, the substantially constant flow rate of the combined liquid is about 40 µL/minute.

Collection and Analysis of Data

In some embodiments, the methods described herein include analyzing the combined liquid with a mass spectrometer to monitor one or more selected m/z ratios. Generally, any mass spectrometer capable of performing the methods described herein may be used, including, but not limited to, those described in the examples.

In some embodiments, the analyzing of the combined liquid with the mass spectrometer includes electrospraying the combined liquid into a triple quadrupole mass spectrometer operating in multiple reaction monitoring mode.

In some embodiments, the methods provided herein utilize a frequency-modulated (FM) approach to sample multiplexing. For example, each sample may be encoded at unique frequencies prior to detection of a total signal by mass spectrometry, and reconstructed ion chromatograms at each m/z of interest may then be a time-dependent signal which is composed of the unique frequencies from each sample. Deconvolution of the RIC by a technique, such as Fourier transform (FT), may reveal the identity of the sample, its relative concentration, or a combination thereof.

In some embodiments, the methods described herein include collecting one or more reconstructed ion chromatograms for one or more selected m/z ratios. As used herein, the phrase "reconstructed ion chromatogram" generally refers to a mass spectrometric data set that includes a mass spectra recorded sequentially in time as the combined liquid is provided to an ion source.

In some embodiments, the methods include analyzing the one or more reconstructed ion chromatograms to determine (i) which of the at least one first analyte, the at least one second analyte, optionally the one or more additional liquids, or a combination thereof contributed to a signal, (ii) the relative concentration of the at least one first analyte, the at least one second analyte, optionally the one or more additional liquids, or a combination thereof that contributed to the signal, or (iii) a combination thereof.

The analyzing of the one or more reconstructed ion chromatograms may be performed using any known technique. For example, the analyzing of the one or more reconstructed ion chromatograms may include subjecting the one or more reconstructed ion chromatograms to fast Fourier transform.

In some embodiments, the analyzing of the one or more reconstructed ion chromatograms reveals one or more time-dependent ion traces, and the method also includes performing spectral deconvolution of the one or more time-dependent ion traces.

In some embodiments, the analytes were analyzed using multiple reaction monitoring (MRM) analysis, which may ultimately result in a limitation of <100 analytes. Generally, MRM analysis includes breaking down an ion of interest in a mass spectrometer, and monitoring multiple product ions of the breakdown, thereby improving confidence regarding the identity of an original ion. In some embodiments, the use of high resolution mass spectrometry could allow for a greater number of analytes to be detected.

Not wishing to be bound by any particular theory, it is believed that the possible necessity for long infusion times and a limited linear dynamic range may be overcome, respectively, by the ease of multiplexing samples without labeling, and the proper adjustment of analyte concentrations.

It is believed that the methods provided herein may be applied in a number of fields, including, but not limited to, the biomedical, pharmaceutical, and environmental sciences.

While certain aspects of conventional technologies have been discussed to facilitate disclosure of various embodiments, applicants in no way disclaim these technical aspects, and it is contemplated that the present disclosure may encompass one or more of the conventional technical aspects discussed herein.

In the descriptions provided herein, the terms "includes," "is," "containing," "having," and "comprises" are used in an open-ended fashion, and thus should be interpreted to mean "including, but not limited to." When methods and systems are claimed or described in terms of "comprising" various components or steps, the systems and methods can also "consist essentially of" or "consist of" the various components or steps, unless stated otherwise.

The terms "a," "an," and "the" are intended to include plural alternatives, e.g., at least one. For instance, the disclosure of "an analyte," "a reconstructed ion chromatogram," "a second liquid," and the like, is meant to encompass one, or mixtures or combinations of more than one analyte, reconstructed ion chromatogram, second liquid, and the like, unless otherwise specified.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

In the examples, the following reagents, methods, equipment, and analysis were used.

Reagents:

LC-MS-grade acetonitrile and water were purchased from Honeywell Burdick & Jackson (Muskegon, Mich.). Formic acid was obtained from ThermoFisher Scientific (Waltham, Mass.). All amino acid standards were obtained from Sigma Aldrich (St. Louis, Mo.); theophylline and caffeine were obtained from Acros Organics (Morris, N.J.).

Multiplexed Flow Experiments:

Syringe pumps (KDS-200, KD Scientific, Holliston, Mass.) were used to deliver reagents to the MS at rates governed by a LabView (National Instruments, Austin, Tex.) program written in-house. Three pumps were used, two of which housed the analytes of interest and the third housed a 50:50 ACN:aqueous 0.1% formic acid mixture. Capillary tubing (Polymicro, Lisle, Ill.) (41 cm length, 150 µm I.D.) was used to connect each sample to a cross (0.25 mm diameter), where the solutions mixed and were delivered through PEEK tubing (Agilent Technologies, Santa Clara, Calif.) (8 cm length, 125 µm I.D.) to the ESI needle (15 cm length, 102 µm I.D.).

Mass Spectrometry Detection:

A TSQ Quantum Access Max triple quadrupole mass spectrometer (ThermoElectron, Walthum, Mass.) was fitted with an ESI source operated in positive mode. Multiple reaction monitoring was performed for the duration of the run on 10 analytes with collection time at 0.1 s for each analyte, and therefore, a continuous collection cycle of 1 s. Analyte fragmentation was monitored using 0.1 s scans for each of the 10 analytes for 35 min. A liquid chromatography pump may be coupled to the triple quadrupole (QqQ) mass spectrometer (Advantage Max, Thermo). The QqQ MS was coupled to the LC system for either conventional bore LC or capillary work using a nano-spray interface. This QqQ MS was capable all typical scans: SRM, MRM, NLS, product or precursor ion scan.

Data Analysis:

Fourier transforms were performed on individual reconstructed ion chromatograms using Origin 2017 (OriginLab, Northhampton, Mass.). Peak heights were obtained using the Peak Analyzer function. Unless otherwise stated, the results are presented as the average of three independent runs and error bars represent ±1 standard deviation. Software for the mass spectrometer was from Thermo: Xcalibur. LC-MS data analysis used Xcalibur to convert ".raw" RICs into ".xls" and Origin to convert the ".xls" into FT/frequency.

Example 1—FM-CFA-ESI-MS Method

The frequency-modulated continuous flow analysis (FM-CFA) system of this example includes the multiplexing of two samples, and is depicted at FIG. 1.

Pumps were used to deliver two samples continuously and directly into a triple quadrupole (QqQ) MS operating in multiple reaction monitoring (MRM) mode. The flow rates from the two samples (S1 and S2) were pulsed independently at unique frequencies (e.g. sinusoidally modulated from 3.3-16.7 µL/min; S1 with a 97-s period and S2 with a 43-s period) and mixed with the output from a third pump.

The output of the third pump also varied in time and was used to maintain a constant flow rate (40 µL/min) into the MS. As the solutions from the pumps combined, the concentration of each sample was encoded at the frequency of each pump, and the resulting signal at each m/z oscillated accordingly.

The frequency domain trace of each reconstructed ion chromatogram (RIC) indicated which sample the analyte belonged to (by the frequency at which it occurred), and its relative concentration (by the peak height).

Therefore, numerous samples could be analyzed by pulsing each at unique frequencies. The limitations of this example included the number of peaks that could be resolved in the frequency domain and the linear dynamic range.

In the FM-CFA-ESI-MS system depicted at FIG. 1, the flow rates of different samples were sinusoidally modulated at non-harmonic frequencies of each other, but the total flow rate to the MS was held constant by inclusion of a make-up flow of buffer. After dilution with the make-up buffer, the concentration of each sample was then encoded at the same frequency as its flow rate. Extraction of the RIC from each analyte m/z yielded time-domain data traces that were then decoded by Fourier analysis. The frequency domain trace indicated the sample from which the peak belonged (by the frequency at which it occurred) and its relative concentration (by the peak height). Therefore, numerous samples were analyzed by pulsing each at unique frequencies.

Specifically, two samples were placed in separate syringe pumps and the flow rates were varied at unique frequencies ($V_{S1}(t)$ and $V_{S2}(t)$, respectively). These solutions met at a cross with flow from a third syringe pump that had a time-dependent velocity used to ensure the total flow rate was kept constant at 40 µL/min.

The top and bottom insets shows the time-dependent flow rate velocities from the two pumps, while the middle inset shows the time-dependent concentration profile that was produced. The combined solution was then subjected to ESI-MS to monitor particular m/z.

Individual RIC were subjected to a fast Fourier transform (FFT) which produced peaks in the frequency domain corresponding to the number of samples. The magnitude of the peaks in the frequency domain was proportional to the analyte concentrations and the frequency of each peak encoded the sample identification.

Figure 2:
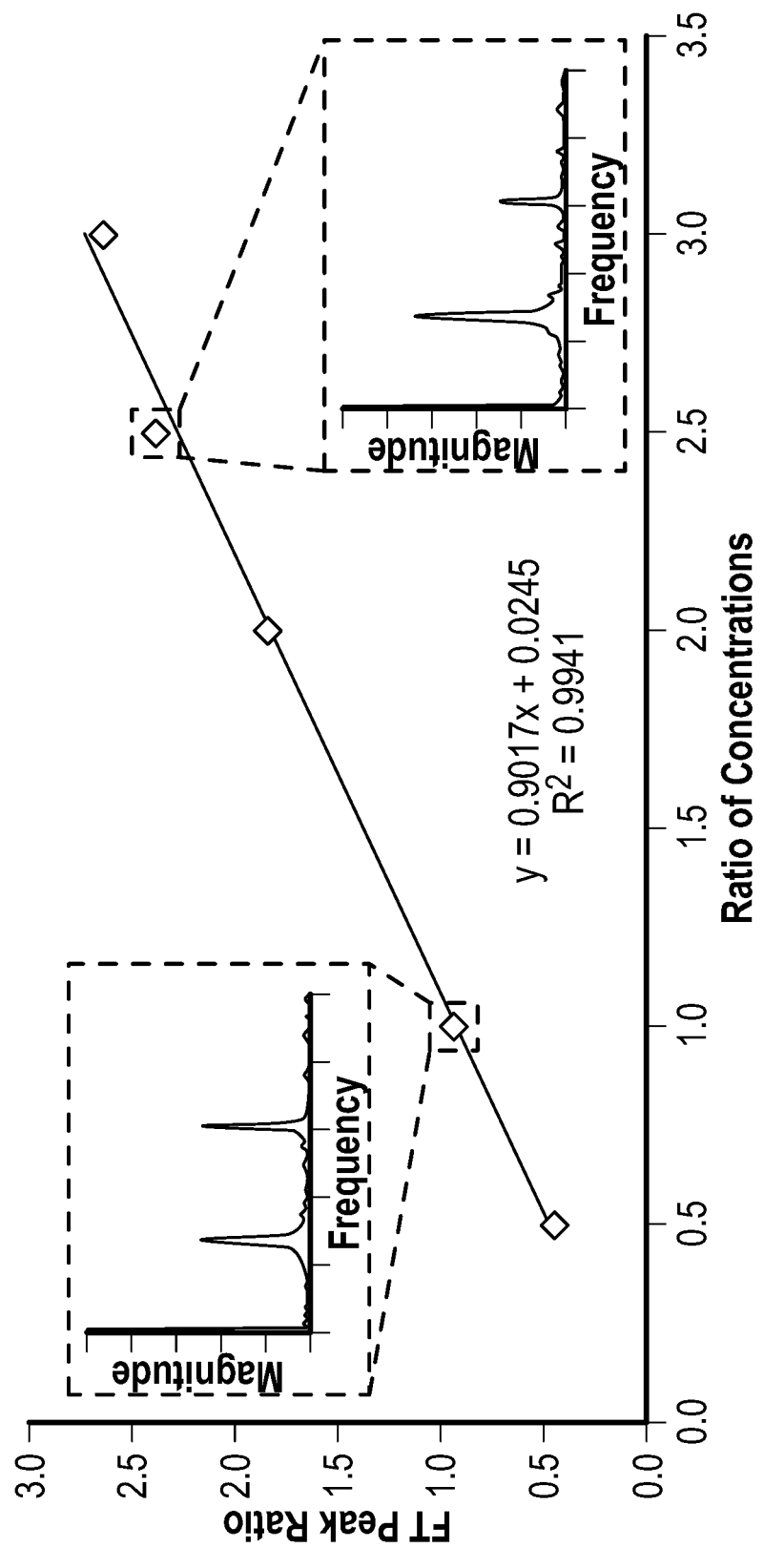
FIG. 2 depicts an embodiment of a calibration curve.

To test this method, caffeine was used as a model analyte with one syringe set to a period of 97 s (0.01 Hz) and at a concentration of 50 µM while the second syringe was set to a period of 43 s (0.023 Hz) and varying concentrations from 25-150 µM were tested. Data were collected for 30 min. FIG. 2 shows the calibration curve obtained by plotting the ratio of FT peak intensity against the ratio of caffeine concentration in each syringe. As explained below, syringe 1 held 50 µM caffeine while syringe 2 contained variable caffeine concentrations from 25 µM to 150 µM. The experimentally measured ratios of the peak heights in the frequency domain are shown on the y-axis while the expected concentration ratio is shown on the x-axis. The insets of FIG. 2 show representative traces from the frequency domain at various concentration ratios.

Specifically, proof of concept for the FM-CFA system of this example was established using caffeine as a model analyte. The flow rate of S1 oscillated from 3.3 µL/min to 16.7 µL/min in a sinusoidal fashion with a period of 97-s (0.01 Hz), while the flow rate of S2 oscillated from 3.3 µL/min to 16.7 µL/min in a sinusoidal fashion at a period of 43-s (0.023 Hz).

The concentration of caffeine in S1 was 125 µM, and the concentration of caffeine in S2 was 50 µM. S2 also contained 50 µM theophylline to act as a frequency fidelity control. The flow rate of syringe 3 (S3) was equal to:

$$\text{Flow rate of } S3 = 40 \text{ µL/min} - (\text{flow rate } S1 + \text{flow rate } S2) \quad (1)$$

The flow rate of S3 ensured that the total flow rate after mixing remained constant. Flow rate control of the syringe pumps was performed using a LabView (National Instruments, Austin, Tex.) program.

An FFT was used to demodulate the RIC at m/z 195 (caffeine) and the peak intensity at 0.01 Hz was found to be ~2.5-fold higher than the peak intensity at 0.023 Hz. This difference in peak height corresponded to the difference in concentrations between the samples in S1 (0.01 Hz) and S2 (0.023 Hz). Examination of the theophylline RIC showed only one peak at the frequency of S2 as expected.

The data showed good linearity with a correlation coefficient >0.99, thereby indicating that this system was capable of quantitating co-infused analytes at different concentrations.

The insets in FIG. 2 show representative traces from the frequency domain at various concentration ratios. The peaks at 0.01 and 0.023 Hz were clearly observed away from low frequency noise. These oscillation periods were chosen to be prime numbers to ensure frequency harmonics would not complicate the data analysis. The peak at lower frequency (S1) had a larger peak width in the frequency domain due to the reduced number of cycles analyzed relative to the higher frequency sample.

The linear dynamic range saturated above a concentration ratio of ~4, which was believed to be due to the difficulty in resolving imperfect sinusoids containing noise in the Fourier transform. It was expected that further optimization of the method and analysis technique can allow a larger linear dynamic range to be employed.

Examination of the frequency domain data indicated $$\frac{1}{f}$$

noise, which was expected. Other frequencies, such as from the oscillatory movement of the syringe pump, were not observed.

Possibly contributing to the success of these experiments was the proper alignment of the capillaries at the mixing tee. When tubing was not flush and properly seated in the tee, one syringe would pull fluid from the second syringe. This attenuated the signals and diminished the quality of the calibration curve. To diagnose this effect, theophylline was added to the sample in syringe 1 and after each analysis, the RIC of theophylline was analyzed. For properly aligned connections, theophylline signal was only present at the frequency of syringe 1 and absent at the frequency of syringe 2. Data which contained theophylline signal at both syringe frequencies were discarded and connections re-aligned.

Example 2—Effect of Period Length and Acquisition

To gain a better understanding of the method of Example 1, the effects of several experimental variables were examined. By increasing the acquisition time of the experiment from 25 minutes to 50 minutes, a decrease in the frequency-domain peak widths occurred.

Figure 5A:
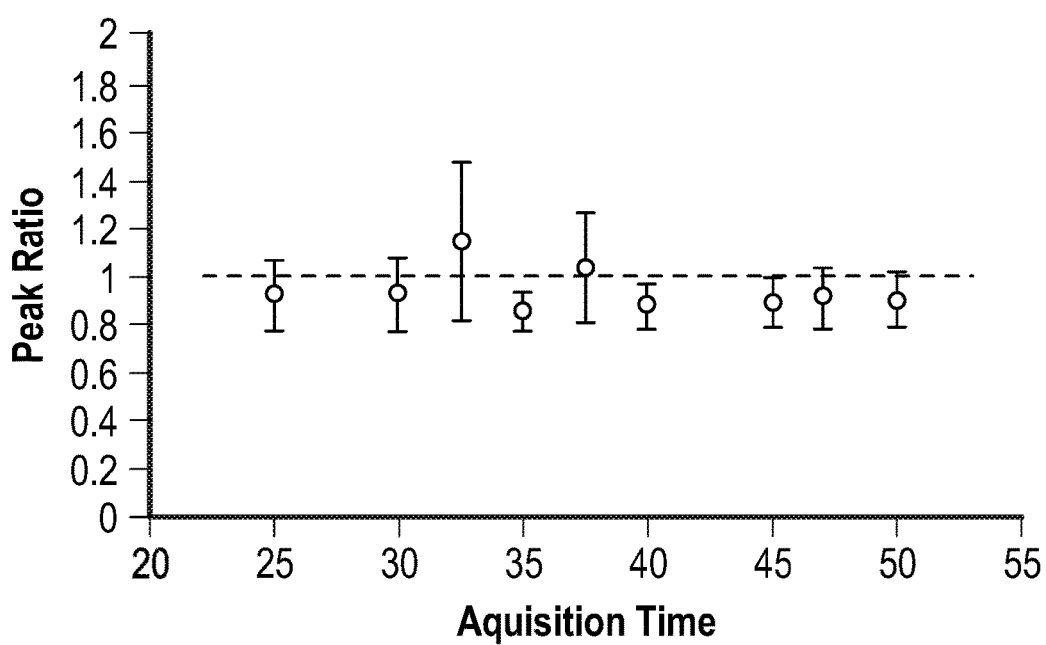
FIG. 5A and FIG. 5B depict plots of peak ratios versus acquisition times for an embodiment of a method described herein.
Figure 5B:
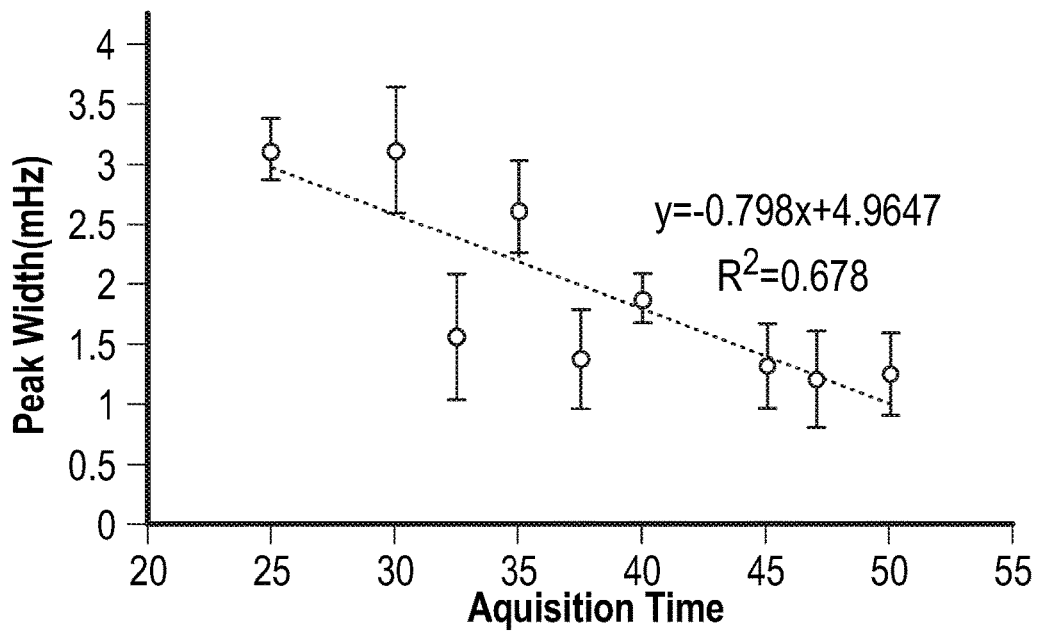

FIG. 5A and FIG. 5B depict the effect of acquisition time on frequency-domain peaks. In both traces, caffeine at a 1:1 concentration ratio was used while the acquisition times varied from 25 minutes to 50 minutes. As depicted at FIG. 5A, the increased acquisition time produced smaller peak widths (full width at half height) in the frequency domain due to increased frequency resolution with more cycles analyzed. As depicted at FIG. 5B, the acquisition time did not significantly affect the measured peak ratio in the frequency domain. The dashed horizontal line of FIG. 5A was set at the expected ratio of 1:1. Each data point was the average value of three independent runs and error bars represent ±1 standard deviation.

While this effect was expected due to increased sampling of the concentration waves, no noticeable changes in the ratio of peak heights were observed.

Another experimental variable tested was the effect of the syringe oscillation period on the measured peak height ratio in the frequency domain. Caffeine was analyzed at a 1:1 concentration ratio while the period of syringe 1 was set at 97 seconds and the period of syringe 2 was varied between 7 seconds and 61 seconds.

Figure 6:
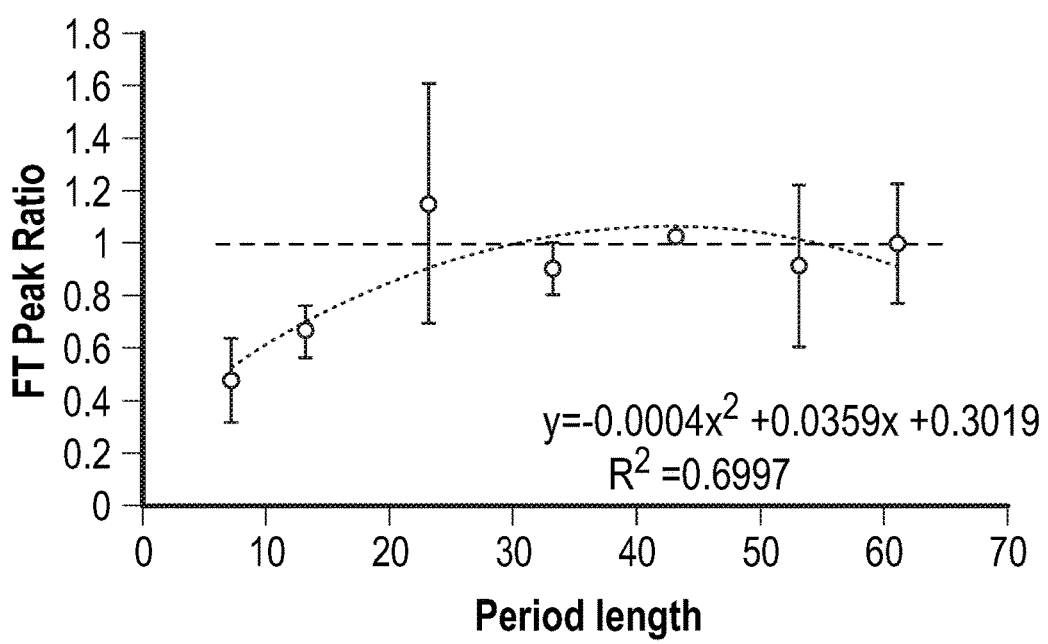
FIG. 6 depicts a plot of peak ratios versus period length for an embodiment of a method described herein.

Higher periods in syringe 2 trended to a frequency domain signal ratio of 1, while lower periods showed a marked decrease in this period ratio, at depicted at FIG. 6. These data suggested that the higher frequency oscillations could not be produced potentially due to limitations with the syringe pumps or with broadening of high frequency pulses as they were delivered to the mass spectrometer.

Specifically, FIG. 6 depicts the effect of the oscillation period on measured peak height ratio. The period of syringe pump 1 was held at 97 seconds and the period of syringe pump 2 was varied at the times shown. The ratio of peak heights in the frequency domain was then plotted as a function of the period of syringe pump 2. When the period of pump 2 was too short, the peak in the frequency domain was lower than that from pump 1, which indicated that these rapid pulses were diluted during transit to the ESI needle. A period greater than 43 seconds offered both an accurate peak ratio and good reproducibility. Each data point was the average value of three independent runs and error bars represent ±1 standard deviation.

Example 3—Development of a Frequency Modulated Continuous Flow Analysis (FM-CFA) Platform In an attempt to improve the linear dynamic range of the system of Example 1, and increase the ability to quantitate multiple analytes simultaneously, one or more sources of non-linearity in the system were uncovered and remedied. This was achieved by determining the input frequency range which could be accurately replicated in the MS data, and establishing the effect of frequency range.

Determining the Input Frequency Range which could be Accurately Delivered in the MS Data:

In one ideal scenario, high frequency oscillations could be used for both S1 and S2. The advantages to high frequency oscillations would include the ability to have more oscillation cycles analyzed during a given acquisition time, which would produce more narrow peaks in the frequency domain. Narrow peaks in the frequency domain can help in quantitation of the peak height ratios.

Figure 7:
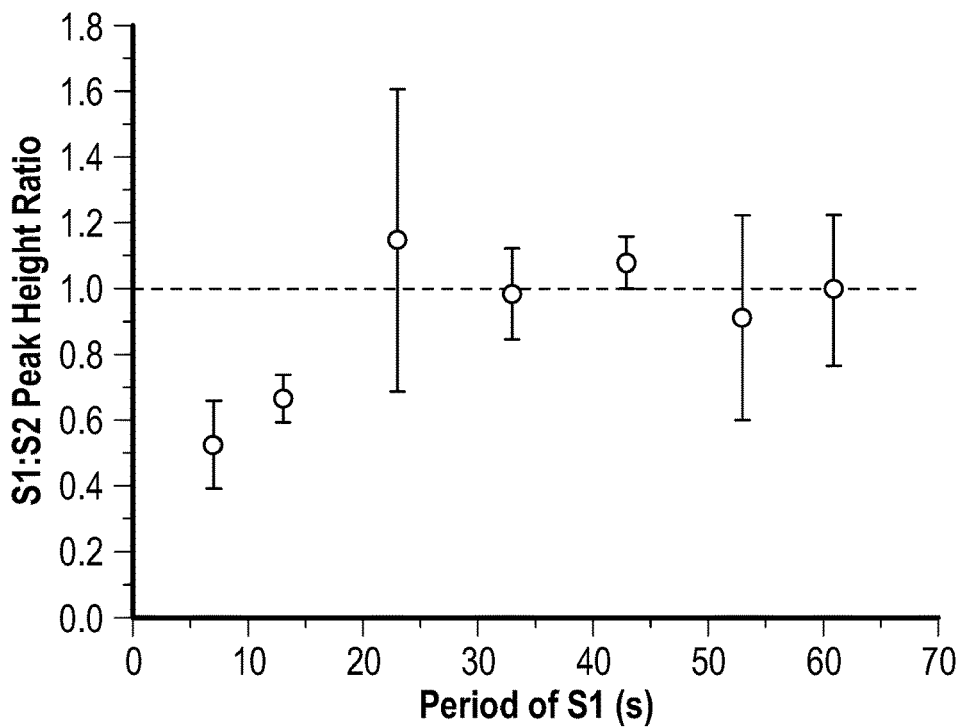
FIG. 7 depicts the effect of oscillation frequency on peak height ratio for an embodiment of a method described herein.

Initial attempts to utilize high frequency oscillations did not produce the expected amplitude ratios. Shown at FIG. 7 is a series of experiments that examined the dependence of syringe oscillation frequency on the measured peak height ratio in the frequency domain.

50 µM caffeine was placed in both S1 and S2, and the period of S2 was set to 97-s, while the period of S1 was varied. As depicted at FIG. 7, when the period of S1 was short (high frequency oscillations), the measured peak height ratio of S1:S2 was less than the expected 1.0. As the oscillation period of S1 increased, the peak height corresponding to S1 increased and the ratio of S1:S2 returned to 1. Therefore, if too short of an oscillation period was used, the measured ratio was not an accurate representation of the concentration ratio, the calibration curve was distorted, and the linear dynamic range (LDR) of the assay was reduced. As described below, the results shown at FIG. 7 are similar to the results of FIG. 8, and the likely reason is the same: dampening of high frequency concentration pulses within the fluid lines. If the effect of this non-linearity is reduced, then it is believed that the LDR of the assay can be increased.

Research Design:

The fluid system is examined to test the range of oscillation periods that can be produced and replicated prior to ESI. Ideally, rapid oscillations from the pumps are used which would allow improvement in the LDR by allowing a large number of oscillation periods to be sampled by the MS over a fixed infusion time. As the number of concentration pulses analyzed by the MS increases, the peaks in the frequency domain will both narrow and increase in S/N, permitting better quantitation of the ratios, as discussed herein.

The dampening of concentration pulses in a liquid stream is analogous to longitudinal diffusion of chromatographic or electrophoretic peaks. This effect may be more troublesome for narrow peaks (produced by high frequency oscillations with pumps) compared to broad peaks (produced by low frequency oscillations) as the effect of diffusion may have a large effect on the amplitude of the former.

In a series of reports, the effect of longitudinal broadening on concentration pulses was described in terms analogous to an electronic lowpass filter since high frequency oscillations become attenuated while low frequency oscillations do not (see Azizi, F. et al., Lab Chip. 2008; 8(6):907-12; and Xie Y, et al., Lab Chip. 2008; 8(5):779-85). To characterize how concentration pulses are attenuated, a cutoff frequency ($f_c$) was defined as the frequency where the amplitude of the output pulses was ~37% (1/e) of the input amplitude. Therefore, to preserve the input oscillation amplitude, the oscillation frequency should stay well below the $f_c$. Importantly, $f_c$ is described in terms of experimental parameters:

$$f_c \sim \left[\frac{V^2}{DL}\right]^{1/2} \quad (2)$$

where V is the average linear velocity, D is the dispersion adjusted diffusion constant, and L is the length traveled. To increase $f_c$ (and thereby allow higher frequency oscillations to be used), a large linear velocity and short distances are desired.

To characterize the system, the $f_c$ of the flow system is determined and increased to allow higher frequencies to be applied. This characterization method has been applied to a different system (see Zhang, X. Y. et al., Anal. Chem., 2010; 82(15):6704-11).

Figure 8:
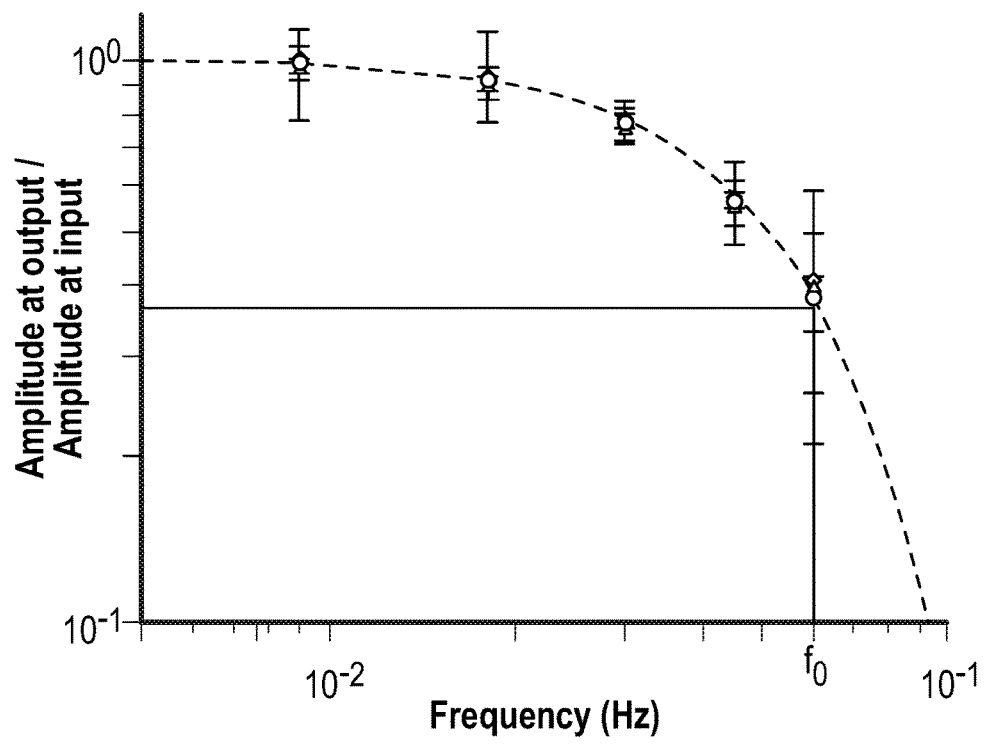
FIG. 8 depicts a plot of amplitude at input/output versus frequency.

Shown at FIG. 8 are measured results of the attenuation of fluorescein pulses within this other system. The dashed line is the best fit curve to an exponential decay function used to describe attenuation. The data trends of FIG. 7 and FIG. 8 are similar (the differences are attributed to the x-axes; plotted are oscillation periods in FIG. 7 and oscillation frequencies in FIG. 8).

FIG. 8 depicts the attenuation of concentration pulses. Specifically, the attenuation of fluorescein pulses in a fluid system was measured and plotted as a function of input frequency. The $f_c$ is defined as the frequency where the attenuation is equivalent to 1/e. This figure is adapted from Zhang X Y, et al., Analytical Chemistry, 2010; 82(15):6704-11.

The $f_c$ of the fluid system is determined using the fluidic system that generated the preliminary data at FIG. 2, FIG. 4A, FIG. 4B, and FIG. 4C. One change to the system is the incorporation of a 4-channel OB1 pressure generator (Elvesys, Paris, France) instead of the syringe pumps to enable fluid flow.

The OB1 uses a piezoelectronic pressure transducer to generate air pressures independently in 4 channels. The air pressure is then delivered to sample reservoirs where the liquid flow rate out of the reservoir is monitored using flow rate sensors (also available from Elvesys). The measured flow rate then feeds back to the OB1 system, creating a closed-loop which allows accurate and precise flow rates to be maintained. These systems are powerful for producing complex timing and delivery of fluids due to their simple programming.

S1 is loaded with 1 µM fluorescein, S2 is loaded with 1 µM Cy5, and S3 is loaded with buffer. At the input and output of each capillary making up the fluid system, the polyimide capillary coatings are removed to facilitate fluorescence detection.

The flow rates of S1 and S2 are sinusoidally modulated with S3 making up the buffer flow. The fluorescence near the input of each channel and at the outputs is measured as a function of the frequency of S1 and S2.

Similar to the results obtained previously in FIG. 8, the attenuation as a function of S1 and S2 input frequency is measured, with attenuation measured as the oscillation amplitude at the output/oscillation amplitude at the input. At low frequencies, this ratio is expected to be ~1 as the amplitudes of the pulses are not significantly different. At high frequencies, the amplitude of the output is reduced and the measured ratio will fall. The frequency at which the ratio of output to input amplitudes is 0.37 determines the $f_c$.

Once the $f_c$ is determined, the linear velocity and capillary lengths are optimized to increase this value. As shown at equation 2, while the highest velocity is desirable, it cannot be increased so high as to reduce the ESI spray efficiency. In a similar fashion, the tubing length cannot be too short such that the output is not completely mixed across the tubing diameter.

The optimal velocity is identified as the highest linear velocity that can be used which maintains good analyte signal response in the MS. Determination of the spatial homogeneity across the tubing diameter is not rigorously examined, except by ensuring the fluorescence and MS signals are reproducible for a given concentration.

After determining the optimized $f_c$, oscillation frequencies are used, at most 0.1*$f_c$, to ensure modest attenuation of all frequencies. As an example, if the optimized $f_c$ is found to be 0.75 Hz, or a 1.3-s period, in experiments, the largest frequency that is applied is 0.075 Hz or a 13-s period.

This characterization is continued as a function of oscillation amplitude as well. This is performed by changing the concentration of fluorescein and Cy5. The data is expected to follow a pattern similar to what is observed elsewhere (see, e.g., Zhang, X. Y. et al., Analytical Chemistry, 2010; 82(15):6704-11.1), where the amplitude of the waves is attenuated to a similar percentage, independent of the concentrations. This is shown at FIG. 8 by the different data points (the amplitudes of the fluorescein pulses were 40, 30, 20, and 10 µM for the different data points at each frequency, respectively).

A major source of attenuation may include the cross tee used to connect the various tubings. Dead volume inside this connection may lead to attenuation that cannot be rectified unless high flow rates are used. Although commercially available "zero dead volume" connections are used, if this piece is a significant source of attenuation, custom connections will be machined to accurately place the outputs of each tubing.

Once these optimizations are performed, the entire system is characterized by using different concentration ratios of the same fluorophore in S1 and S2. The resulting output pattern should match theoretical curves of the summation of two waves. For example, a 1 µM fluorescein solution is placed in S1 and S2, and the period of S1 set to 30-s, while the period of S2 set to 47-s. The output fluorescence signal is transformed into the frequency domain and the ratio of the peak heights at periods of 30- and 47-s should be 1. The oscillation periods are then varied while the output ratio is examined. It is expected that the ratio in the frequency domain will remain 1 as long as the oscillation frequencies are $\leq 0.1*f_c$.

Finally, the amplitude ratio of fluorescein in S1 and S2 is examined. For example, the fluorescein concentration is fixed at 1 µM in S1 and varied in S2. The ratio of the peaks in the frequency domain should match the ratio of concentrations in S1 and S2, as long as the rule of $0.1*f_c$ is maintained.

Following the determination of optimal fluidic conditions, the system is tested with a ThermoFisher Advantage Max QqQ-MS on multi-analyte samples. In the first experiment, caffeine is used as a representative analyte and its concentration is fixed at 5 µM in S1. In S2, varying concentrations of caffeine, up to 20-fold in either direction, are used. After optimization of the $f_c$, the LDR of the calibration curve will be larger than that shown at FIG. 2.

Figure 4A:
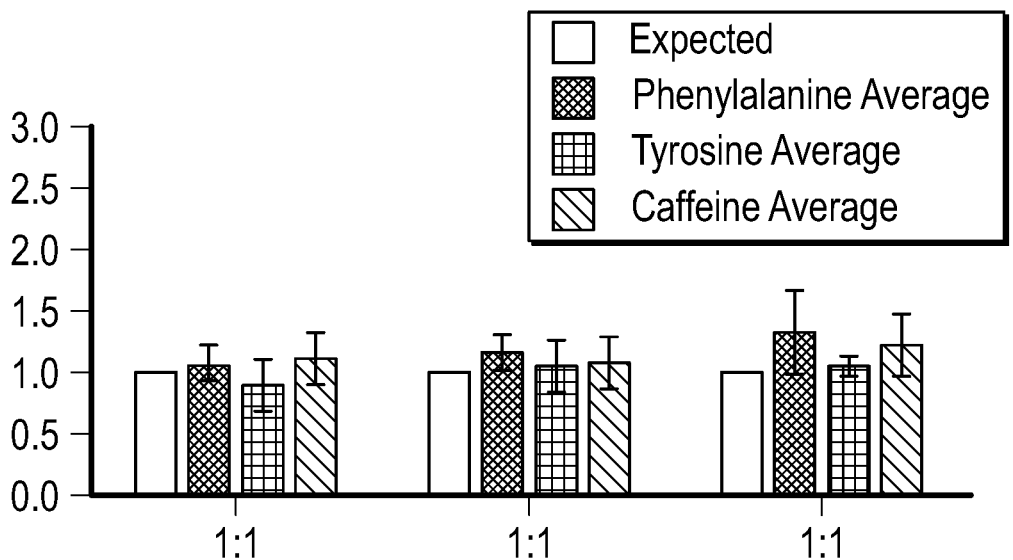
FIG. 4A, FIG. 4B, and FIG. 4C depict the results of an embodiment of a method for analyzing multiple analytes.
Figure 4B:
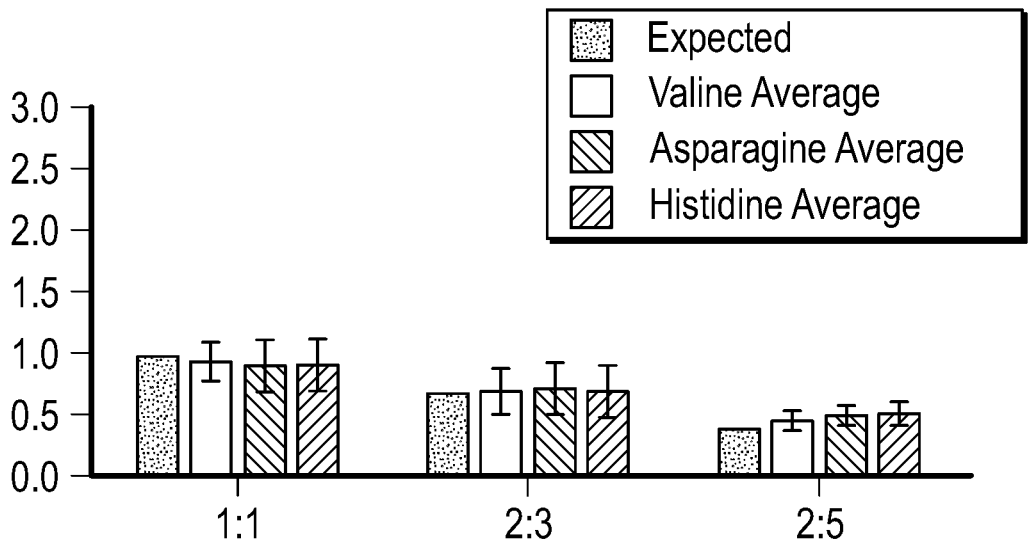
Figure 4C:
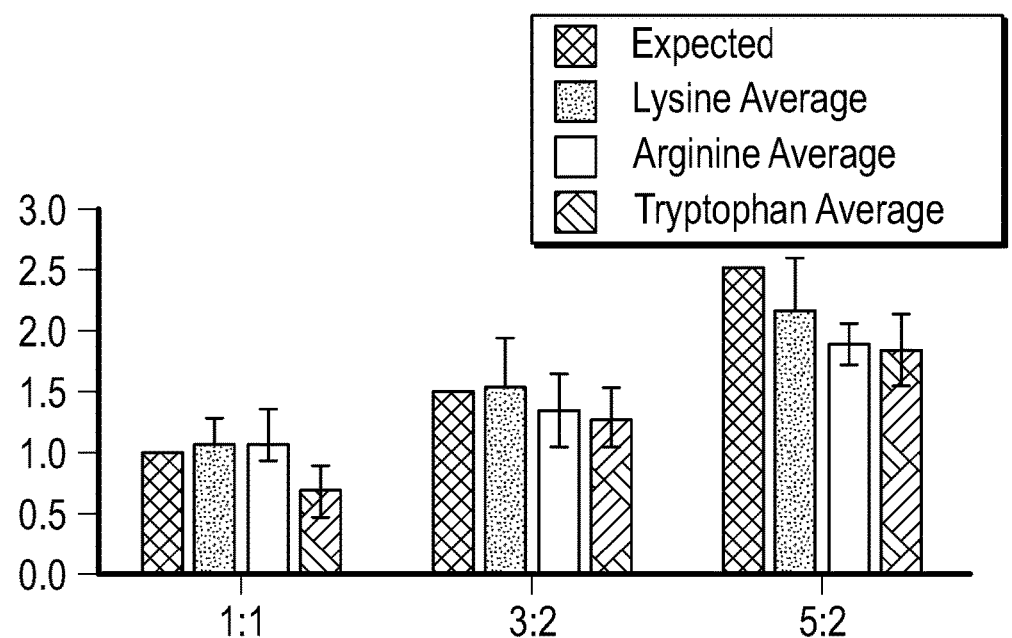

After this initial test with a single analyte, the robustness of the system is tested by increasing the number of analytes examined to the 9 used in FIG. 4A, FIG. 4B, and FIG. 4C. The concentration for all 9 analytes in S1 is held constant at 5 µM and the concentrations randomized from 250 nM to 100 µM in S2. The LDR is expected to be independent of the analyte and similar to that found in the single analyte case. For all experiments, the frequencies of S1 and S2 are unique and both will be $\leq 0.1*f_c$.

For all experiments, theophylline in S2 is used as a check to ensure the flow of one sample does not affect the flow of the other sample (i.e., in the RIC for theophylline, there should only be the S2 frequency observed).

Determine the Role of Resolution on Linear Dynamic Range in FM-CFA:

The LDR of the FM-CFA system is improved beyond the current 4:1 concentration ratio (see FIG. 2) once the optimum $f_c$ is established, as previously described. A similar dynamic range of current isotopic and isobaric tagging methods (~20:1) is obtained. Besides improving the fluidic system as described herein, another approach to increase the LDR is to increase the resolution and S/N of the peaks in the frequency domain. This is especially applicable at the low and high end of the calibration curve: more resolution is needed for better quantitation of peaks with disparate heights. The minimum resolution and S/N of the peaks in the frequency domain that are required for accurate quantitation of peak heights are determined.

Research Design:

Resolution in the frequency domain is partly determined by the optimum oscillation frequencies described above. The effect of peak width is examined by keeping the oscillation frequency constant, and varying the acquisition time. A preliminary examination of the effect of increasing acquisition time on the peaks in the frequency domain yielded data that is to be expected with Fourier analysis (FIG. 9A, FIG. 9B, FIG. 9C).

As seen, extending the acquisition time from 10- to 30-min yielded a decrease in the peak width due to the sampling of increased number of oscillation cycles. This decrease in peak width resulted in improved resolution in the frequency domain and improved quantitation of peak heights. This improvement in quantitation was observed when, during initial work on the preliminary data, a 15-min acquisition time was utilized for the data at FIG. 2 which resulted in only a 3:1 LDR. After increasing the acquisition time to 35-min, the LDR increased to the current 4:1. This simple change in the acquisition time, which may be further optimized, resulted in a large improvement in the LDR. In addition, FIG. 9A, FIG. 9B, and FIG. 9C demonstrate that there was ample peak capacity such that more samples at other frequencies can be used.

Figure 9A:
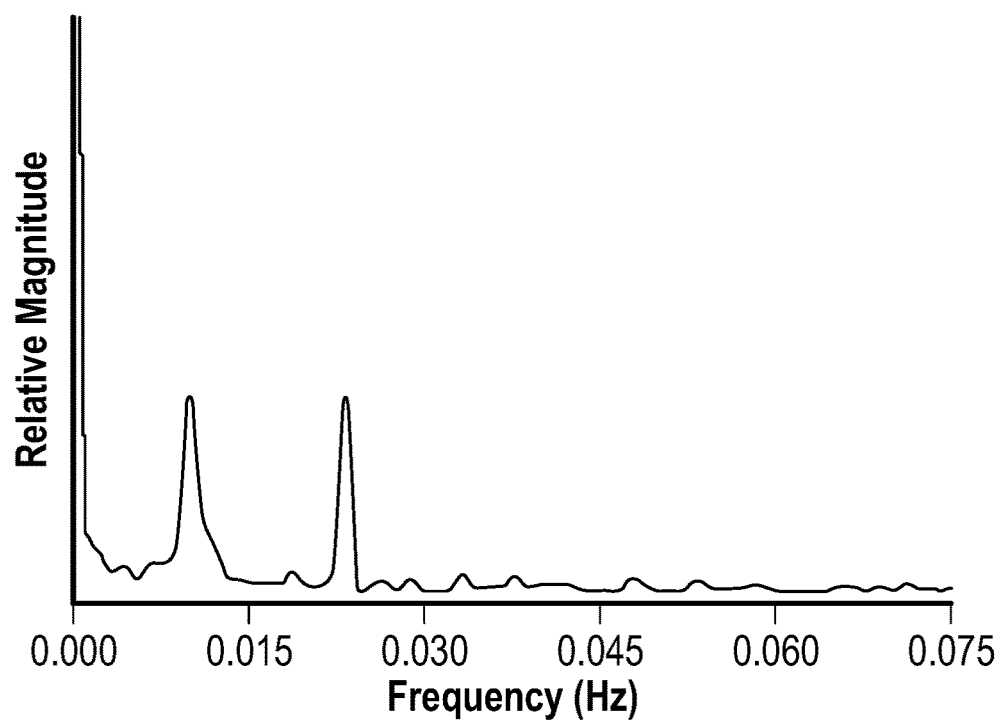
FIG. 9A, FIG. 9B, and FIG. 9C depict the effect of acquisition time on frequency domain peaks for embodiments described herein.
Figure 9B:
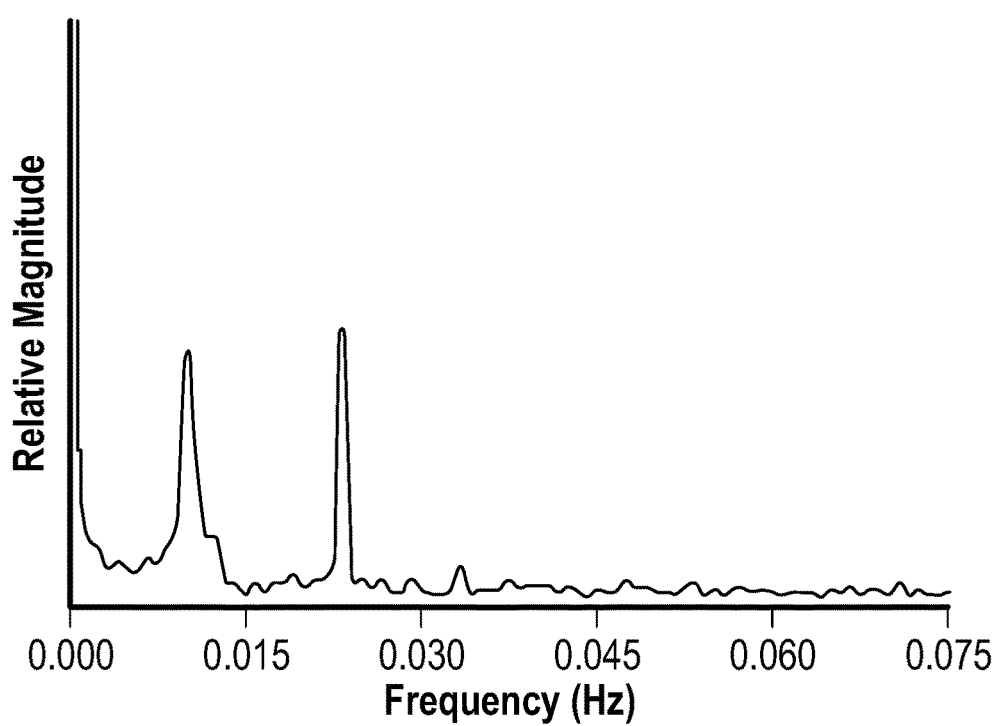
Figure 9C:
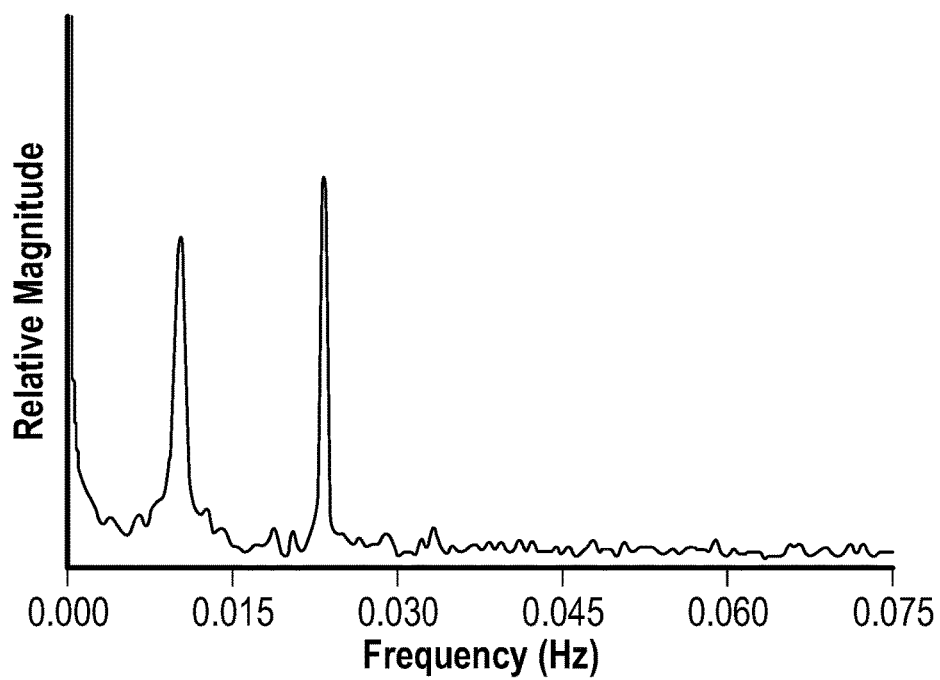

Specifically, FIG. 9A, FIG. 9B, and FIG. 9C depict the effect of Acquisition Time on Frequency Domain Peaks. To collect the data, 100 µM caffeine was placed in S1 and S2. S1 was oscillated with a 97-s period and S2 with a 43-s period. Data from the QqQ-MS were acquired for (FIG. 9A) 10-minutes, (FIG. 9B) 20-minutes, and (FIG. 9C) 30-minutes. The resulting three FFT traces of the RIC at 197 m/z are shown and indicate better resolution and S/N in the frequency domain as the acquisition time increased.

To fully characterize the effects of acquisition time on resolution in the frequency domain, an acquisition time of 60-min is used with caffeine as the model analyte at a 1:1 concentration ratio in S1:S2. The data is truncated in 5-min segments to evaluate the effect of different acquisition times on resolution. These experiments extend to include larger and smaller concentration ratios between S1 and S2. Using this data, calibration curves are generated to quantify the relationship between LDR and frequency resolution. The peak widths eventually converge to a minimum value at some time before 60-min due to other experimental or data analysis factors.

The effect of increased acquisition time affects the peak widths in the frequency domain, and also increases the S/N of the peaks. As seen at FIG. 9A, FIG. 9B, and FIG. 9C, the longer acquisition times also significantly reduced the noise in the frequency domain without greatly affecting the absolute signal. Therefore, the experiments outlined above to identify the minimum acquisition time on peak width are used to identify the minimum acquisition time for achieving a maximum S/N. Again, the S/N may asymptotically improve to a particular value, set by other experimental or analysis parameters, as the acquisition time increases.

Determine the Effect of Salt on Signal Ratio in FM-CFA:

Due to limited charge in the electrospray droplet, high salt may lead to signal suppression and competing ionization. Because salt and matrix effects vary between samples of interest, salt effects have the potential to strongly influence the quantitative ability of any ESI-MS based system.

The systems of the examples herein resisted salt effects between batch samples.

The FM-CFA system of this example was investigated to determine the degree to which it is resistant to quantitation from salt effects.

Three analytes, lysine, arginine, and caffeine, were analyzed simultaneously by conventional flow injection analysis-ESI-MS and the new FM-CFA-ESI-MS method.

Figure 10A:
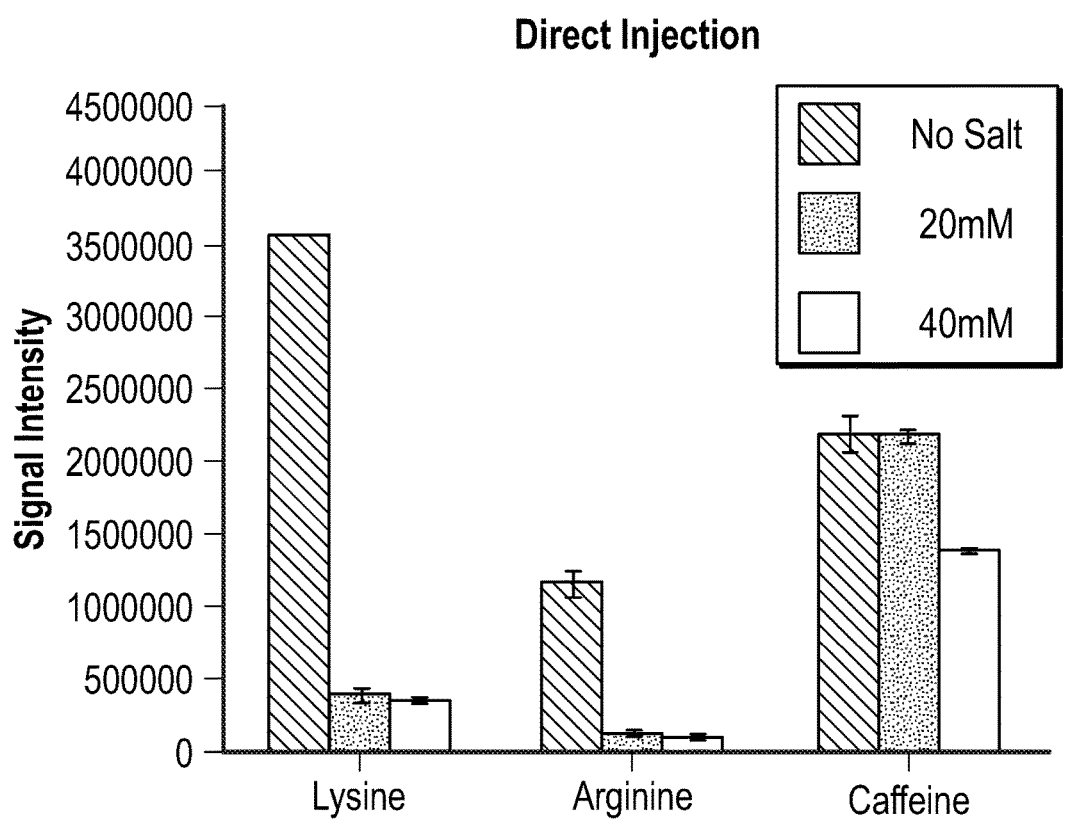
FIG. 10A and FIG. 10B depict the effect of salt on embodiments of quantitation.

FIG. 10A shows conventional flow injection analysis of these three analytes in a 50:50 ACN:water mixture with 0, 20, or 40 mM ammonium formate. As expected, the three analytes showed a marked decline in signal upon the salt addition. The new FM-CFA-ESI-MS method (FIG. 10B) was performed by placing the same analyte mixture into both S1 and S2 (at 1:1 concentration ratio), with S1 containing 0 mM salt and varying the salt concentration in S2. When the signals from these analytes were examined, the ratio of peak heights in the frequency domain were not significantly different compared to the no salt condition ($p>0.05$).

Figure 10B:
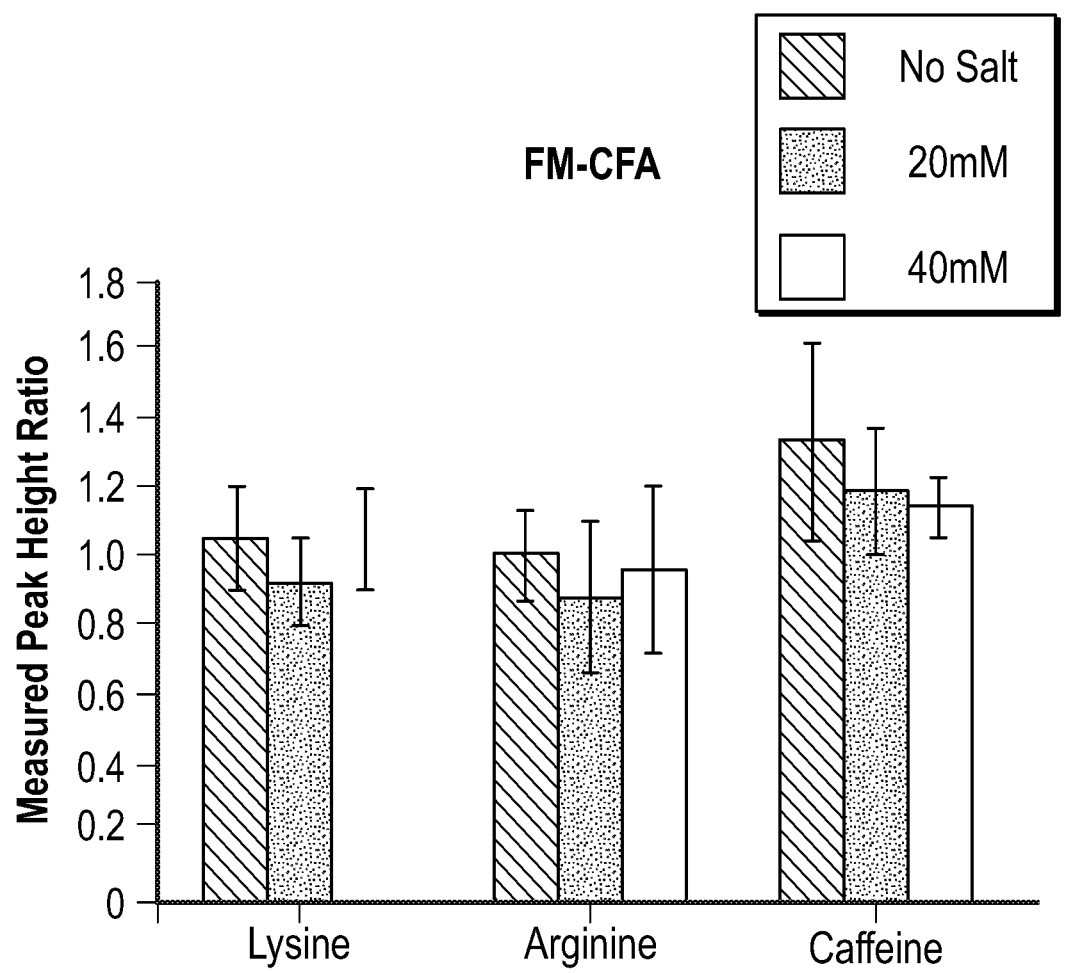

Specifically, FIG. 10A and FIG. 10B depict the effect of salt on quantitation. 25 µM samples of lysine, arginine, and caffeine were directly injected into an ESI needle and analyzed by MRM with and without the ammonium formate concentration shown in the legend (FIG. 10A). The same analytes were placed in both S1 and S2, while the salt concentration in S2 was varied as shown in the legend and analyzed via FM-CFA-ESI-MS (FIG. 10B). The concentration ratio for each analyte was 1:1.

These data strongly suggested that FM-CFA can quantitate under high salt concentrations. This effect was attributed to analytes in both syringes being exposed to the same salt environment during electrospray.

These experiments are further expanded to test the range of analytes as well as the limit of salt concentration. Using the 9 analytes from FIG. 4A, FIG. 4B, and FIG. 4C, matrix effects on the frequency domain ratios of S1 and S2 are determined.

Experiments containing a variety of analyte concentration ratios in S1:S2 are used with salt concentrations of 5, 25, 50, and 125 mM in S2. The highest salt concentrations are identified that can be used until the coefficient of determination ($R^2$) for the calibration curve (similar to FIG. 2) diminishes below 0.95.

Upon determination of this maximum amount of salt, the FM-CFA technique is applied to real world, complex samples. A diluted sample of amino acids in serum (NIST SRM 1950) is used in S1, and neat amino acid standards are used in S2 at concentrations near the reported values. This experiment is repeated using serial dilutions of the serum mixture to evaluate the ability to quantify in this complex matrix.

If one syringe contains a complex matrix and the other contains a solution of neat standards, the quantitation between the two should still hold. This is because the streams are mixed and undergo the same amount of competing ionization at the same time. As such, it will be resistant to the diminished quantitation which plagues most direct injections of complex samples.

Example 4—Multiple Analytes

The system of Example 1 (see FIG. 1) was used to quantitate a number of analytes within a sample. In this example, nine analytes (caffeine, arginine, lysine, tryptophan, phenylalanine, tyrosine, valine, asparagine, histidine) were analyzed simultaneously by placing all 9 in both S1 and S2 (theophylline also in S2), but at different concentration ratios.

In experiment 1, the concentration ratio of all 9 analytes were 1:1 (S1:S2). In experiment 2, the concentration ratios of phenylalanine, tyrosine, and caffeine were 1:1, while the concentration ratios of lysine, arginine, and tryptophan were increased to 3:2, and valine, asparagine, histidine were decreased to 2:3 (S1:S2). Experiment 3 was similar to experiment 2 but used a larger range of concentration ratios 5:2 and 2:5, for the increased and decreased samples, respectively.

Figure 3:
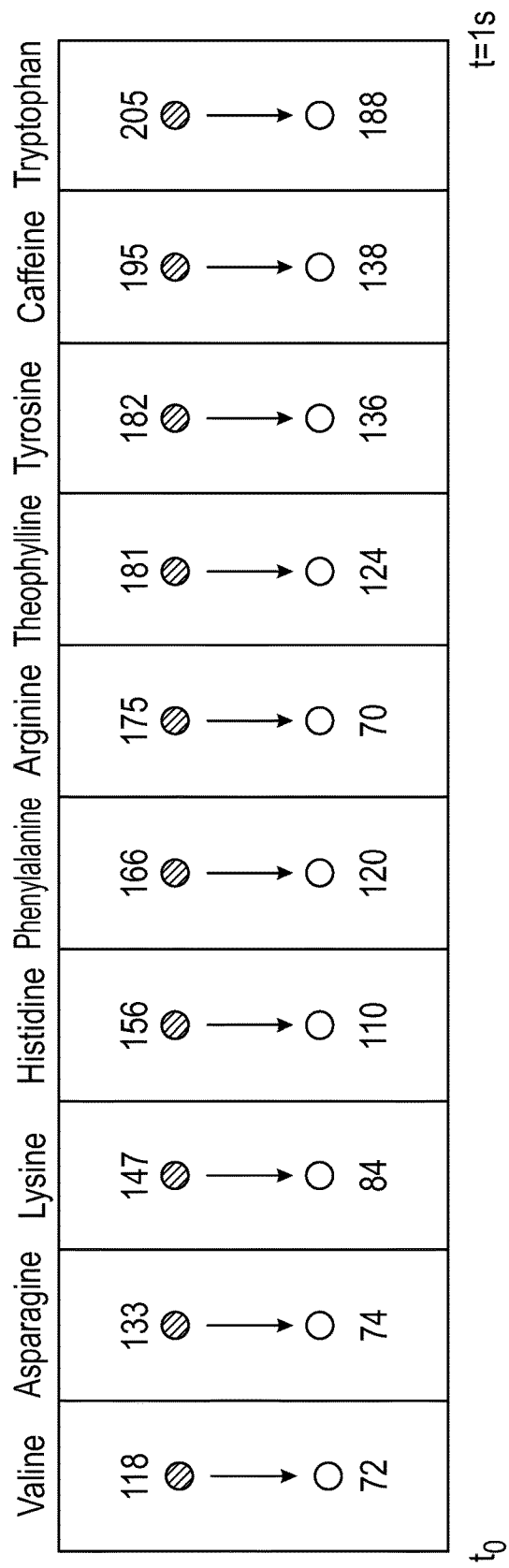
FIG. 3 depicts the multiple reaction monitoring (MRM) transitions monitored in one embodiment of a method described herein.

FIG. 3 depicts the multiple reaction monitoring (MRM) transitions monitored in the 9-plex experiments of this example. The precursor and product ion m/z that were monitored are shown at FIG. 3, and each m/z was monitored for 0.1 s for a total time of 1 s.

FIG. 4A, FIG. 4B, and FIG. 4C summarize the results of the measured peak height ratios for the various analytes whose concentrations were held constant (FIG. 4A), decreased (FIG. 4B), and increased (FIG. 4C). For all analytes tested, the peak ratios in the frequency domain followed the expected trend. The measured frequency domain peak ratios are plotted as a function of the expected concentration ratio in S1:S2 for: FIG. 4A—1:1 concentration ratios of phenylalanine, tyrosine, and caffeine; FIG. 4B—1:1, 2:3, and 2:5 concentration ratios of valine, asparagine, and histidine; and FIG. 4C—1:1, 3:2, and 5:2 concentration ratios of lysine, arginine, and tryptophan. Theophylline was kept in S2 to ensure oscillation fidelity.

The methods of this example were robust in their relative quantitation even when analyte concentrations were 6.5-times different. Quantitation was found to be more robust with longer acquisition times of the experiment and oscillation periods of the samples. Due to the combination of the samples, there was little effect of salt on the relative quantitation ability of this method.

Example 5—Develop Sequential Throughput and Parallel Multiplexing Capabilities in FM-CFA Two variations of FM-CFA are used to test the limits of sample throughput: parallel and serial multiplexing. The throughput goal for parallel multiplexing is 5 min/sample, while the fully automated sequential system has a goal of 144 samples/day.

Parallel Multiplexing of 7 Samples:

Described above is the multiplexing of 2 samples. This number is increased through the use of more oscillation frequencies and a zero-dead volume interface to combine the various flows.

To demonstrate the feasibility of using FM-CFA for parallel analysis of more than 2 samples, while minimizing costs and maintaining automation, stepper motors are used to control the height of 7 samples (S1-S7) and one buffer (S8) and flow is driven by gravity. The flow rate is dependent on the height of the sample, the viscosity of the solution, and the length of the tubing.

These stepper motors are inexpensive and are automated through LabView programs. The flow rates from each sample are calibrated to the height of the reservoir prior to experiments using standards and measuring the time it takes to see a change in signal after a change in height.

The flow from the 8 reservoirs is combined in a custom "zero dead volume" interface. A 3D printer or micromachining in poly(dimethyl siloxane) or glass is used to build the device.

The output of the device is coupled to an ESI needle for spraying into the MS. At no time do the sample heights fall below the tee, which may cause flow to move back towards the samples. There is positive displacement from the samples with flow rates oscillating from 0.3 to 1.7 µL/min at unique frequencies.

As the number of samples increases, the total flow rate is constant after the various solutions merge. To test the stability, a commercially-available sensor is used to monitor the flow rate prior to the ESI needle. Spectral analysis of the data indicates no frequency components of the final mixed solution. If necessary, the flow is imaged in the mixing tee using appropriate combinations of fluorophores and camera. For example, fluorescein may be disposed in S1, S3, S5, and S7, and Cy5 may be disposed in S2, S4, and S6. This is done if problems are observed in the stability of the flow rates from each sample.

Initial samples include the analytes used to generate FIG. 4A, FIG. 4B, and FIG. 4C, and each are placed in a separate sample container. A combination of oscillation frequencies is tested with prime numbers a preferred choice to avoid overlaps with harmonics in the frequency domain. For example, if all samples are at the same concentration, similar peak heights can be observed in the frequency domain at 0.079, 0.053, 0.043, 0.037, 0.031, 0.023, and 0.017 Hz.

While initially oscillation frequencies $\leq 0.1 * f_c$ are used, the amplitudes are monitored in the frequency domain and ensure that they match with the expected concentration values. If these do not match, the new cutoff frequencies are determined and oscillation frequencies below this value are used. Due to the proximity of the peaks in the frequency domain, it is preferred to have high resolution for quantitation. To help ensure narrow peak widths in the frequency domain, the 7 analytes are infused into the MS for at least 35-min. The optimal run time is determined by a similar procedure as described in the previous example.

After these initial characterizations, more complicated samples are attempted in order to test the limits of the system. Standard solutions of the 9 analytes used in FIG. 4A, FIG. 4B, and FIG. 4C at different concentrations and different levels of background salts are placed into each syringe and infused. This tests the ability to quantitate samples with disparate matrices.

Serial Multiplexing of 144 Samples:

To achieve high throughput in analyses and high level of quantitation, a serial, automated sample introduction system is used. The goal of this sequential FM-CFA system is the analysis of 144 samples in 24-h without user input.

To perform this assay, a sample is introduced into an oscillating carrier stream via an autoinjector. This sample is mixed with a set of analyte standards of known concentration oscillating at a different frequency. This sample and set of standards are equivalent to S1 and S2, respectively, and they mix with a make-up flow (analogous to S3) to maintain a constant flow rate prior to being sprayed into the MS for analysis.

The time-dependent RIC curves for each m/z reveal two frequencies, one corresponding to S1 and one corresponding to S2 with their amplitudes providing quantitative information. Samples are sequentially introduced into the oscillating carrier stream using the autoinjector and can be of various matrix composition, as FIG. 10A and FIG. 10B indicate that the FM-CFA method is resistant to differences in salt concentrations between S1 and S2.

Liquids are driven by the OB1 pressure controller from Elvesys while monitoring the flow rate. The velocity of S1 is varied in time producing flow rate oscillations and coupled directly to the autosampler on a Nanomate HPLC pump. The autosampler is set to bypass the HPLC.

The autosampler loop is adjustable and will be set to 50 µL enabling each sample to be analyzed for ~10-min at an average flow rate of 5 µL/min. The volume of sample actually injected is dependent on the optimum flow rate found in the previous example, but a minimum of 10 min analysis time per sample is chosen (this time could be increased to decrease peak widths in the frequency domain).

Since the entire flowpath is composed of open tubes, the resistance to flow is low and the use of the OB1, which has a maximum pressure output of 8 bar, should not be problematic. At 10-min per sample, the system is able to analyze 144 samples per day with minimal user input, a high level of quantitation, and relatively inexpensive front-end equipment.

Experiments lasting >8-h (up to 24-h) are performed to ensure reproducible flow rates and injections using caffeine as the model standard. Due to the closed-loop control of the flow rate with the OB1, no problems are anticipated. After this initial characterization, the system is tested with more complex samples in more complex matrices to determine the broader impacts of this method. For example, one complex sample includes the measurement of organic contaminants in human serum. A mixture of 12 perfluorinated acids in methanol (NIST SRM 8446) is used in S2, offering high signal due to the hydrophobicity of these compounds.

The samples that are injected by the autosampler (S1) include perfluorinated acids found in diluted sludge (NIST SRM 1958) or diluted human serum (NIST SRM 2781). Another complex sample includes amino acids in human plasma (NIST SRM 1950). The amino acids are evaluated by comparison to a 1:1000 dilution of butyl esterified amino acids in acidified methanol. The values found are matched against the certified NIST values. By analyzing replicate series of each of these samples, the effects of competing ionization, durability of the system, precision, and accuracy are determined. The sensitivity of the QqQ-MS run in MRM mode is sufficient to detect the approximate concentrations of the perfluorinated acids (high nM for sludge and mid nM for serum).

We claim:

1. A method of analysis, the method comprising:
   providing a first liquid at a first flow rate that is varied at a first frequency, wherein the first liquid comprises at least one first analyte;
   providing a second liquid at a second flow rate that is varied at a second frequency, wherein the second liquid comprises at least one second analyte, and wherein the first frequency and the second frequency are different;
   combining the first liquid and the second liquid with a third liquid to form a combined liquid, wherein the third liquid has a time-dependent velocity effective to impart the combined liquid with a substantially constant flow rate;
   analyzing the combined liquid with a mass spectrometer to monitor one or more selected m/z ratios;
   collecting one or more reconstructed ion chromatograms for the one or more selected m/z ratios; and
   analyzing the one or more reconstructed ion chromatograms to determine (i) which of the at least one first analyte, the at least one second analyte, or a combination thereof contributed to a signal, (ii) the relative concentration of the at least one first analyte, the at least one second analyte, or a combination thereof that contributed to the signal, or (iii) a combination thereof.

2. The method of claim 1, wherein the analyzing of the one or more reconstructed ion chromatograms comprises:
   subjecting the one or more reconstructed ion chromatograms to Fourier transform.

3. The method of claim 1, wherein the analyzing of the one or more reconstructed ion chromatograms reveals one or more time-dependent ion traces, and the method further comprises:
   performing spectral deconvolution of the one or more time-dependent ion traces.

4. The method of claim 1, wherein the analyzing of the combined liquid with the mass spectrometer comprises:
electrospraying the combined liquid into a triple quadrupole mass spectrometer operating in multiple reaction monitoring mode.

5. The method of claim 1, wherein the providing of the first liquid comprises:
sinusoidally modulating the first flow rate from (i) about 1 µL/minute to about 5 µL/minute to (ii) about 12 µL/minute to about 18 µL/minute with a period of about 90 seconds to about 110 seconds.

6. The method of claim 1, wherein the providing of the first liquid comprises:
sinusoidally modulating the first flow rate from 3.3 µL/minute to about 16.7 µL/minute with a period of about 97 seconds.

7. The method of claim 1, wherein the providing of the second liquid comprises:
sinusoidally modulating the second flow rate from (i) about 1 µL/minute to about 5 µL/minute to (ii) about 12 µL/minute to about 18 µL/minute with a period of about 30 seconds to about 50 seconds.

8. The method of claim 1, wherein the providing of the second liquid comprises:
sinusoidally modulating the second flow rate from 3.3 µL/minute to about 16.7 µL/minute with a period of about 43 seconds.

9. The method of claim 1, wherein the substantially constant flow rate of the combined liquid is about 1 µL/minute to about 100 µL/minute.

10. The method of claim 1, wherein the substantially constant flow rate of the combined liquid is about 20 µL/minute to about 60 µL/minute.

11. The method of claim 1, wherein the substantially constant flow rate of the combined liquid is about 40 µL/minute.

12. The method of claim 1, further comprising:
providing one or more additional liquids, wherein each of the one or more additional liquids comprises one or more additional analytes, and each of the one or more additional liquids has a flow rate that is varied at a unique frequency that differs from (i) the first frequency and (ii) the second frequency; and
combining the one or more additional liquids with the third liquid to form the combined liquid.

13. The method of claim 1, wherein the first liquid, the second liquid, or both the first liquid and the second liquid comprise 2 to 300 analytes.

14. The method of claim 1, wherein the at least one first analyte and the at least one second analyte are identical.

15. The method of claim 14, wherein the at least one first analyte and the at least one second analyte are present in the first liquid and the second liquid, respectively, at different concentrations.

16. The method of claim 1, wherein the third liquid comprises a buffer.

17. The method of claim 1, wherein the at least one first analyte, the at least one second analyte, or a combination thereof is independently selected from an amino acid.

* * * * *